United States Patent [19]

Yang

[11] 4,054,738
[45] Oct. 18, 1977

[54] SODIUM CEFAMANDOLE CRYSTALLINE FORMS

[75] Inventor: Kuo S. Yang, Indianapolis, Ind.

[73] Assignee: Eli Lilly and Company, Indianapolis, Ind.

[21] Appl. No.: 642,922

[22] Filed: Dec. 22, 1975

[51] Int. Cl.$^2$ ............................................. C07D 501/36
[52] U.S. Cl. ............................................. 544/26
[58] Field of Search ............................. 260/243 C

[56] References Cited

U.S. PATENT DOCUMENTS

| | | | |
|---|---|---|---|
| 3,496,171 | 2/1970 | Pfeiffer et al. | 260/243 C |
| 3,641,021 | 2/1972 | Ryan | 260/243 C |
| 3,692,781 | 9/1972 | Oughton | 260/243 C |
| 3,819,620 | 6/1974 | Dürsch et al. | 260/243 C |
| 3,862,186 | 1/1975 | Silvestri | 260/243 C |
| 3,928,592 | 12/1975 | Greene et al. | 260/243 C |

*Primary Examiner*—Nicholas S. Rizzo
*Assistant Examiner*—David E. Wheeler
*Attorney, Agent, or Firm*—William B. Scanlon; Everet F. Smith

[57] ABSTRACT

Sodium 7-(D-2-hydroxy-2-phenylacetamido)-3-(1-methyl-1H-tetrazole-5-ylthiomethyl)-3-cephem-4-carboxylate is obtained as a pharmaceutically acceptable crystalline anhydrate via crystalline methanolate or crystalline monohydrate forms.

3 Claims, No Drawings

SODIUM CEFAMANDOLE CRYSTALLINE FORMS

BACKGROUND OF THE INVENTION

The cephalosporin antibiotic 7-(D-2-hydroxy-2-phenylacetamido)-3-(1-methyl-1H-tetrazole-5-ylthiomethyl)-3-cephem-4-carboxylic acid represented by the structural formula

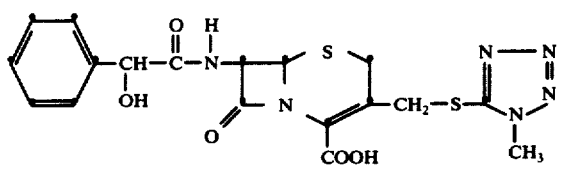

is described by Ryan in U.S. Pat. No. 3,641,021. This antibiotic, referred to herein as cefamandole, is a potent broad spectrum parenteral antibiotic with excellent activity against infectious microorganisms of the gram-negative type. Although cefamandole can be readily prepared, it has been difficult to obtain a pharmaceutically acceptable salt of cefamandole in a crystalline form of sufficient stability and purity suitable for parenteral administration.

Extensive development work on the antibiotic has afforded the O-formyl ester of cefamandole sodium salt in the gamma crystalline form as described in copending application Ser. No. 567,324, filed Apr. 11, 1975. This crystalline form of the O-formyl derivative of cefamandole sodium is suitable for parenteral administration; however, it is best administered when formulated with a mild base such as sodium carbonate. Such formulations are described in copending U.S. application Ser. No. 444,622, filed Feb. 21, 1974, now Pat. No. 3,928,592, issued Dec. 23, 1975.

A stable, crystalline form of sodium cefamandole suitable for bulk preparation and administration would avoid the necessity of preparing the O-formyl derivative form and would thus simplify the production of the antibiotic.

This invention provides a crystalline anhydrate of sodium cefamandole which is readily prepared and which possesses the stability characteristics desirable in formulations of the antibiotic.

This invention also provides a crystalline methanolate and a crystalline monohydrate of sodium cefamandole. These forms are useful as intermediate crystalline structures in the preparation of the anhydrate of sodium cefamandole.

DETAILED DESCRIPTION

The crystalline anhydrate of sodium cefamandole is a white microcrystalline solid which is best characterized by its X-ray powder diffraction pattern shown below. The diffraction pattern was obtained with nickel filtered copper radiation (Cu:Ni) of wave length $\lambda = 1.5405\text{A}$. The interplanar spacings are in the column headed by "d" and the relative intensities in the column headed "$I/I_1$."

| Spacing d | Relative Intensity $I/I_1$ |
|---|---|
| 14.24 | .61 |
| 12.70 | .22 |
| 8.14 | .15 |
| 7.92 | .23 |
| 7.25 | .71 |
| 6.60 | .15 |
| 6.43 | .30 |
| 5.33 | .13 |
| 5.06 | .12 |
| 4.83 | .55 |
| 4.29 | .29 |
| 4.17 | .15 |
| 4.02 | .26 |
| 3.64 | .12 |
| 3.60 | .13 |
| 3.58 | .12 |
| 3.50 | .05 |
| 3.42 | .06 |
| 3.28 | .07 |
| 3.20 | .08 |
| 3.14 | .06 |
| 2.96 | .09 |
| 2.87 | .21 |
| 2.80 | .06 |
| 2.72 | .15 |
| 2.67 | .08 |
| 2.57 | .07 |
| 2.52 | .04 |
| 2.41 | .12 |
| 2.29 | .15 |

Stability studies carried out thus far on the crystalline anhydrate demonstrate substantially no loss in either antibiotic activity or in crystallinity when the salt is maintained for 1 week at 60° C.

This invention also provides the crystalline methanolate and monohydrate forms of sodium cefamandole. Both of these novel forms can be used to prepare the crystalline anhydrate as discussed hereinafter.

The crystalline methanolate, alternatively referred to herein as the methanol solvate, is characterized by its X-ray powder diffraction pattern shown below. The pattern was obtained using nickel filtered copper radiation (Cu:Ni) of wave length $\lambda 1.5405\text{A}$ to calculate the interplanar spacings and the relative intensities.

| Spacing d | Relative Intensity $I/I_1$ |
|---|---|
| 15.22 | .06 |
| 14.24 | 1.00 |
| 12.99 | .25 |
| 8.75 | .18 |
| 7.92 | .19 |
| 7.65 | .45 |
| 7.16 | .46 |
| 6.93 | .25 |
| 6.62 | .18 |
| 5.48 | .15 |
| 5.30 | .07 |
| 5.11 | .26 |
| 4.98 | .47 |
| 4.79 | .40 |
| 4.64 | .19 |
| 4.22 | .08 |
| 4.15 | .07 |
| 3.76 | .11 |
| 3.89 | .28 |
| 3.70 | .18 |
| 3.58 | .19 |
| 3.49 | .22 |
| 3.35 | .13 |
| 3.12 | .09 |
| 2.93 | .06 |
| 2.89 | .17 |
| 2.79 | .10 |
| 2.76 | .08 |
| 2.66 | .09 |
| 2.56 | .07 |

The methanolate form contains about 6.0 percent by weight of methanol which corresponds to a mole ratio of methanol to sodium cefamandole of 1:1.

The crystalline methanol solvate can be prepared by crystallizing substantially pure amorphous sodium cefamandole from methyl alcohol. Alternatively, the methanolate can be prepared with cefamandole acid by converting the acid in methyl alcohol to sodium cefamandole with the sodium salt of a weak acid. The sodium cefamandole precipitates from solution as the crystalline methanolate. Salts of weak acids which can be used include, for example, sodium acetate, sodium propionate, sodium 2-ethylhexanoate, and like sodium salts of weak carboxylic acids which are soluble in methanol.

The methanol solvate crystalline form is preferably prepared with substantially pure cefamandole in the free acid form as follows. The cefamandole acid is dissolved in methyl alcohol, and a solution of excess sodium acetate in methyl alcohol is added to the solution. The solution of sodium acetate is added slowly to avoid gel formation and addition is halted when the pH reaches about 6. The solution thus obtained (crystallization solution) is allowed to stand to complete crystallization. The crystals of methanol solvate are filtered and washed with a suitable dry organic solvent, for example ethanol or diethyl ether, and then are allowed to dry.

The crystallization procedure for the methanol solvate can be carried out at a temperature between about 0° and 50° C. The preferred temperature range of crystallization is between 15° and 40° C. Over the preferred temperature range yields of the methanolate crystalline form are generally between about 90 and 95 percent. At temperatures much above 40° C. the yields are usually lower. For example, at a crystallization temperature of about 50° C., yields of methanolate are about 60 percent.

The crystallization of the methanol solvate is preferably carried out under substantially anhydrous conditions. Although trace or minor amounts of water in the crystallization solution have no deleterious effect on the yields of methanolate crystals, larger amounts can result in the formation of hydrated crystalline forms along with the methanol solvate form. Accordingly, for best results the crystallization is carried out with dry methanol and with anhydrous sodium acetate. Reagent grade methanol and anhydrous sodium acetate are also preferred over less pure grades.

The methanol solvate is obtained in highest yields from a concentrated crystallization solution. Therefore, concentrated solutions of cefamandole free acid in methanol and of anhydrous sodium acetate in methanol are used to form the concentrated crystallization solution of sodium cefamandole. A suitable concentration of cefamandole acid in methanol is about one gram of the antibiotic acid per 2–3 ml. of methanol. A concentrated solution of anhydrous sodium acetate in methanol containing about 1 g. of anhydrous sodium acetate per 12 ml. of methanol can be conveniently prepared at room temperature as follows. Excess anhydrous sodium acetate is stirred in methanol for several minutes and the undissolved salt is filtered. The filtrate can then be used to form the crystallization solution with the methanol solution of cefamandole free acid.

Methyl alcohol is unique in its ability to form a crystalline solvate of sodium cefamandole. Attempts to prepare crystalline forms of sodium cefamandole with other alcohols have led to the formation of amorphous salt. For example, when in the above described preparation for the methanolate, methyl alcohol is replaced with ethyl alcohol, amorphous sodium cefamandole is obtained rather than an ethanol solvate.

The methanol solvate is the precursor crystalline form for both the anhydrate and monohydrate crystalline forms described herein. The methanol of crystallization of the methanolate form can be removed in vacuo to provide the anhydrate crystalline form or, alternatively, the methanol of crystallization can be displaced by water to form the crystalline monohydrate form.

The crystalline monohydrate of sodium cefamandole contains about 4 percent by weight of water which corresponds to a ratio of water to sodium cefamandole of 1:1. The monohydrate crystalline structure differs from that of both the anhydrate and the methanolate. The X-ray powder diffraction pattern of the monohydrate is shown below. Again, nickel filtered copper radiation of wave length λ1.5405A was used.

| Spacing d | Relative Intensity $I/I_1$ |
|---|---|
| 13.79 | .57 |
| 12.23 | .40 |
| 8.23 | .12 |
| 7.52 | .09 |
| 7.21 | .40 |
| 7.02 | .60 |
| 6.67 | .15 |
| 6.19 | .25 |
| 5.09 | .10 |
| 4.84 | .42 |
| 4.70 | .33 |
| 4.15 | .37 |
| 3.99 | .26 |
| 3.84 | .08 |
| 3.76 | .09 |
| 3.65 | .12 |
| 3.55 | .10 |
| 3.40 | .08 |
| 3.25 | .10 |
| 3.07 | .11 |
| 2.92 | .06 |
| 2.76 | .16 |
| 2.65 | .11 |
| 2.62 | .05 |
| 2.49 | .15 |
| 2.41 | .05 |
| 2.36 | .07 |
| 2.23 | .11 |

The monohydrate is prepared with the above-described methanol solvate by allowing water to displace the methanol of crystallization in the methanolate crystals. The preparation of the monohydrate is carried out by exposing the methanolate crystals to moist air. The displacement of methanol with water occurs at a convenient rate at a relative humidity of between about 40 and 60 percent at a temperature between about 20° and 30° C. The preferred conditions are 50 percent relative humidity at 25° C. The preparation of the monohydrate crystalline form is conveniently carried out in this manner in a humidity chamber.

The monohydrate is less stable than the anhydrate. It becomes discolored and loses some antibiotic activity as well as undergoing crystalline disfiguration in the standard stability test carried out at 60° C. for 1 week.

The previously described crystalline anhydrate of sodium cefamandole can be prepared with either the monohydrate or preferably with the methanol solvate. The water of crystallization of the monohydrate or the methanol of crystallization of the methanol solvate are removed under reduced pressure to provide the anhydrate crystalline form.

The conversion of the methanol solvate to the anhydrate crystalline form is carried out under vacuum at a temperature between about 25° and 45° C. and preferably at about 40° C.

The monohydrate crystalline form can be dehydrated under vacuum at a temperature between about 45° and 50° C. to form the anhydrate. Preferably, a drying agent is placed in the vacuum oven to increase the rate of anhydrate formation.

The monohydrate will lose water at room temperature at 0 percent relative humidity; however, the rate is much slower than when dehydration is carried out as described above.

The anhydrate form of sodium cefamandole will rehydrate to the monohydrate crystalline form if exposed to moist air. For example, at a relative humidity of about 55 percent at about 25° C., the anhydrate absorbs about 40 percent by weight of water in less than an hour. Accordingly, the anhydrate crystalline form is stored prior to use in sealed containers or in a dry atmosphere to prevent the formation of the less stable monohydrate form.

The anhydrate or the monohydrate can be converted to the methanolate crystalline form by crystallization from dry methyl alcohol.

The conversion of the three crystalline forms of sodium cefamandole into one another as discussed above is illustrated by the following triangular diagram.

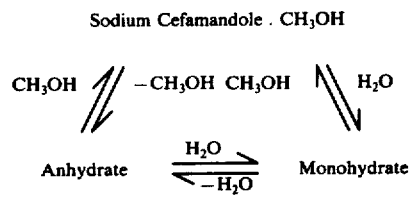

The crystalline anhydrate can be stored in bulk form in closed containers for subsequent formulation. Alternatively, it can be prepared in unit dosage form in sealed ampoules for parenteral administration in the treatment of infectious diseases. The crystalline monohydrate and the crystalline methanol solvate are intermediate crystalline forms useful for preparing the anhydrate form.

The following examples are provided to further illustrate the present invention.

EXAMPLE 1

Sodium Cefamandole Methanolate

To a solution of 100 g. of cefamandole acid in approximately 200 ml. of methyl alcohol was slowly added a solution of 25 g. of anhydrous sodium acetate in 300 ml. of methyl alcohol until the pH of the solution reached pH 6. The solution was allowed to stand at room temperature until crystallization of the methanolate crystalline form was complete. The crystals were harvested by filtration through a Buchner funnel and were washed with dry ethyl alcohol and with diethyl ether.

EXAMPLE 2

Sodium Cefamandole Anhydrate

A solution of cefamandole acid in methanol was prepared by dissolving 4.0 kg. of cefamandole acid in 8.8 l. of methyl alcohol with stirring. To the solution was added with vigorous stirring a solution of 0.98 kg. of anhydrous sodium acetate in 9.0 l. of methyl alcohol. The rate of addition of the sodium acetate solution was about 0.25 liters per minute. After addition was completed, the crystal slurry was stirred for 1 hour. The crystals of methanol solvate were then harvested on a Buchner funnel and were washed with a mixture of 1 liter of methanol and 1 liter of ethanol on the filter. The washed crystals were transferred to drying pans and spread in a thin layer. The drying pans were placed in a Stokes oven and the crystals dried under vacuum (28 inches Hg.) at a temperature of about 40° C. The dried crystals of anhydrate were transferred to amber glass jars which were sealed for storage.

EXAMPLE 3

Sodium Cefamandole Monohydrate

Ten grams of sodium cefamandole methanolate crystals, prepared as described by Example 1, were exposed at room temperature to approximately a 50 ± 10 percent relative humidity for about 16 hours to provide 9.8 g. (quantitative yield) of sodium cefamandole monohydrate crystals.

I claim:

1. The crystalline anhydrate of sodium 7-(D-2-hydroxy-2-phenylacetamido)-3-(1-methyl-1H-tetrazole-5-ylthiomethyl)-3-cephem-4-carboxylate which has the following X-ray powder diffraction pattern obtained with nickel filtered copper radiation of $\lambda 1.5405 \text{Å}$ wherein $d$ represents the interplanar spacing and $I/I_1$ the relative intensity.

| Spacing d | Relative Intensity $I/I_1$ |
|---|---|
| 14.24 | .61 |
| 12.70 | .22 |
| 8.14 | .15 |
| 7.92 | .23 |
| 7.25 | .71 |
| 6.60 | .15 |
| 6.43 | .30 |
| 5.33 | .13 |
| 5.06 | .12 |
| 4.83 | .55 |
| 4.29 | .29 |
| 4.17 | .15 |
| 4.02 | .26 |
| 3.64 | .12 |
| 3.60 | .13 |
| 3.58 | .12 |
| 3.50 | .05 |
| 3.42 | .06 |
| 3.28 | .07 |
| 3.20 | .08 |
| 3.14 | .06 |
| 2.96 | .09 |
| 2.87 | .21 |
| 2.80 | .06 |
| 2.72 | .15 |
| 2.67 | .08 |
| 2.57 | .07 |
| 2.52 | .04 |
| 2.41 | .12 |
| 2.29 | .15 |

2. The crystalline methanol solvate of sodium 7-(D-2-hydroxy-2-phenylacetamido)-3-(1-methyl-1H-tetrazole-5-ylthiomethyl)-3-cephem-4-carboxylate which consists of approximately 6 percent by weight of methanol and which has the following X-ray powder diffraction pattern obtained with nickel filtered copper radiation of 1.5405Å wherein $d$ represents the interplanar spacing and $I/I_1$ the relative intensity.

| Spacing d | Relative Intensity $I/I_1$ |
|---|---|
| 15.22 | .06 |
| 14.24 | 1.00 |
| 12.99 | .25 |
| 8.75 | .18 |
| 7.92 | .19 |

-continued

| Spacing d | Relative Intensity $I/I_1$ |
|---|---|
| 7.65 | .45 |
| 7.16 | .46 |
| 6.93 | .25 |
| 6.62 | .18 |
| 5.48 | .15 |
| 5.30 | .07 |
| 5.11 | .26 |
| 4.98 | .47 |
| 4.79 | .40 |
| 4.64 | .19 |
| 4.22 | .08 |
| 4.15 | .07 |
| 3.76 | .11 |
| 3.89 | .28 |
| 3.70 | .18 |
| 3.58 | .19 |
| 3.49 | .22 |
| 3.35 | .13 |
| 3.12 | .09 |
| 2.93 | .06 |
| 2.89 | .17 |
| 2.79 | .10 |
| 2.76 | .08 |
| 2.66 | .09 |
| 2.56 | .07 |

3. The crystalline monohydrate of sodium 7-(D-2-hydroxy-2-phenylacetamido)-3-(1-methyl-1H-tetrazole-5-ylthiomethyl)-3-cephem-4-carboxylate which consists of approximately 4 percent by weight of water and which has the following X-ray powder diffraction pattern obtained with nickel filtered copper radiation of $\lambda 1.5405 \text{Å}$ wherein $d$ represents the interplanar spacing and $I/I_1$ the relative intensity.

| Spacing d | Relative Intensity $I/I_1$ |
|---|---|
| 13.79 | .57 |
| 12.23 | .40 |
| 8.23 | .12 |
| 7.52 | .09 |
| 7.21 | .40 |
| 7.02 | .60 |
| 6.67 | .15 |
| 6.19 | .25 |
| 5.09 | .10 |
| 4.84 | .42 |
| 4.70 | .33 |
| 4.15 | .37 |
| 3.99 | .26 |
| 3.84 | .08 |
| 3.76 | .09 |
| 3.65 | .12 |
| 3.55 | .10 |
| 3.40 | .08 |
| 3.25 | .10 |
| 3.07 | .11 |
| 2.92 | .06 |
| 2.76 | .16 |
| 2.65 | .11 |
| 2.62 | .05 |
| 2.49 | .15 |
| 2.41 | .05 |
| 2.36 | .07 |
| 2.23 | .11 |

* * * * *